US011147540B2

(12) United States Patent
Meyering et al.

(10) Patent No.: US 11,147,540 B2
(45) Date of Patent: Oct. 19, 2021

(54) INTRODUCER SHEATH AND PUNCTURE TOOL FOR THE INTRODUCTION AND PLACEMENT OF A CATHETER IN TISSUE

(71) Applicant: Minnetronix, Inc., St. Paul, MN (US)

(72) Inventors: Emily Rolfes Meyering, St. Louis Park, MN (US); Elizabeth Scheurer, Minneapolis, MN (US); Aaron McCabe, Edina, MN (US)

(73) Assignee: Minnetronix, Inc., St. Paul, MN (US)

( * ) Notice: Subject to any disclaimer, the term of this patent is extended or adjusted under 35 U.S.C. 154(b) by 354 days.

(21) Appl. No.: 15/184,454

(22) Filed: Jun. 16, 2016

(65) Prior Publication Data

US 2017/0000361 A1 Jan. 5, 2017

Related U.S. Application Data

(60) Provisional application No. 62/187,460, filed on Jul. 1, 2015.

(51) Int. Cl.
*A61B 10/00* (2006.01)
*A61M 39/22* (2006.01)
(Continued)

(52) U.S. Cl.
CPC .......... *A61B 10/0045* (2013.01); *A61B 46/10* (2016.02); *A61B 90/40* (2016.02); *A61M 39/10* (2013.01); *A61M 39/223* (2013.01); *A61B 2010/0077* (2013.01); *A61B 2017/3492* (2013.01); *A61M 2039/1033* (2013.01); *A61M 2039/229* (2013.01)

(58) Field of Classification Search
CPC ........ A61M 27/006; A61M 2210/0693; A61M 2202/0464; A61M 25/0111; A61F 2007/126; A61B 10/0045
See application file for complete search history.

(56) References Cited

U.S. PATENT DOCUMENTS 2,969,066 A 1/1961 Holter et al.
3,419,010 A 12/1968 Williamson
(Continued)

FOREIGN PATENT DOCUMENTS

CA 2407214 A1 4/2003
CA 2597293 A1 8/2006
(Continued)

OTHER PUBLICATIONS

Park et al., "Continuous Dielectrophoretic Bacterial Separation and Concentration from Physiological Media of High Conductivity," The Royal Society of Chemistry, Lab Chip, 2011, pp. 2893-2900, vol. 11.
(Continued)

*Primary Examiner* — Patrick Fernandes
(74) *Attorney, Agent, or Firm* — Seager, Tufte & Wickhem, LLP (57) ABSTRACT

Disclosed embodiments include methods and devices for introducing a sheath into a human or animal subject. Some embodiments include a puncture tool that may simultaneously deliver a sheath and a needle to a desired anatomical location. The needle may be removed and the sheath may be used to define a space that may be used to conduct a procedure.

15 Claims, 4 Drawing Sheets

(51) Int. Cl.
  *A61M 39/10* (2006.01)
  *A61B 90/40* (2016.01)
  *A61B 46/10* (2016.01)
  *A61B 17/34* (2006.01)

(56) References Cited

U.S. PATENT DOCUMENTS

| | | |
|---|---|---|
| 3,867,937 A | 2/1975 | Schwartz |
| 3,889,687 A | 6/1975 | Harris et al. |
| 3,900,026 A * | 8/1975 | Wagner ................ A61M 25/02 128/888 |
| 4,378,797 A | 4/1983 | Osterholm |
| 4,446,154 A | 5/1984 | Osterholm |
| 4,451,251 A | 5/1984 | Osterholm |
| 4,551,137 A | 11/1985 | Osborne |
| 4,686,085 A | 8/1987 | Osterholm |
| 4,767,409 A | 8/1988 | Brooks |
| 4,830,849 A | 5/1989 | Osterholm |
| 4,888,115 A | 12/1989 | Marinaccio et al. |
| 4,904,237 A | 2/1990 | Janese |
| 4,950,232 A | 8/1990 | Ruzika et al. |
| 4,958,901 A | 9/1990 | Coombs |
| 4,989,614 A * | 2/1991 | Dejter, Jr. ........... A61B 10/0283 600/565 |
| 5,061,246 A * | 10/1991 | Anapliotis ............. A61B 46/10 206/210 |
| 5,160,323 A | 11/1992 | Andrew |
| 5,171,226 A | 12/1992 | McCrory |
| 5,190,529 A | 3/1993 | McCrory et al. |
| 5,250,035 A * | 10/1993 | Smith ................ A61B 17/3401 604/168.01 |
| 5,332,092 A * | 7/1994 | Fischer ................ A61M 5/002 206/305 |
| 5,334,315 A | 8/1994 | Matkovich et al. |
| 5,358,495 A * | 10/1994 | Lynn ................ A61M 25/0111 604/163 |
| 5,396,899 A | 3/1995 | Strittmatter |
| 5,405,316 A | 4/1995 | Magram |
| 5,423,738 A | 6/1995 | Robinson et al. |
| 5,462,667 A | 10/1995 | Wollinsky et al. |
| 5,496,281 A * | 3/1996 | Krebs ................ A61M 25/065 604/168.01 |
| 5,531,673 A | 7/1996 | Helenowski |
| 5,601,727 A | 2/1997 | Bormann et al. |
| 5,683,357 A | 11/1997 | Magram |
| 5,752,942 A * | 5/1998 | Doyle ................ A61M 5/3286 604/274 |
| 5,755,968 A | 5/1998 | Stone |
| 5,772,607 A | 6/1998 | Magram |
| 5,836,928 A | 11/1998 | Gerber et al. |
| 5,897,528 A | 4/1999 | Schultz |
| 5,941,853 A | 8/1999 | Collins |
| 5,947,689 A | 9/1999 | Schick |
| 5,948,441 A | 9/1999 | Lenk et al. |
| 5,980,480 A | 11/1999 | Rubenstein et al. |
| 6,013,051 A | 1/2000 | Nelson |
| 6,056,725 A | 5/2000 | Elsberry |
| 6,217,552 B1 | 4/2001 | Barbut et al. |
| 6,238,382 B1 | 5/2001 | Schock et al. |
| 6,264,625 B1 | 7/2001 | Rubenstein et al. |
| 6,326,044 B1 | 12/2001 | Lindquist |
| 6,379,331 B2 | 4/2002 | Barbut et al. |
| 6,383,159 B1 | 5/2002 | Saul et al. |
| 6,383,380 B1 | 5/2002 | Kopf |
| 6,387,290 B1 | 5/2002 | Brody et al. |
| 6,468,219 B1 | 10/2002 | Njemanze |
| 6,537,241 B1 | 3/2003 | Odland |
| 6,558,353 B2 | 5/2003 | Zohmann |
| 6,575,928 B2 | 6/2003 | Saul et al. |
| 6,594,880 B2 | 7/2003 | Elsberry |
| 6,641,563 B1 | 11/2003 | Vitullo et al. |
| 6,682,508 B1 | 1/2004 | Meythaler et al. |
| 6,689,085 B1 | 2/2004 | Rubenstein et al. |
| 6,689,756 B2 | 2/2004 | Hesson et al. |
| 6,699,269 B2 | 3/2004 | Khanna |
| 6,709,426 B2 | 3/2004 | Gijsbers et al. |
| 6,758,832 B2 | 7/2004 | Barbut et al. |
| 6,830,561 B2 | 12/2004 | Jansen et al. |
| 6,849,185 B1 | 2/2005 | Wu et al. |
| 6,875,192 B1 | 4/2005 | Saul et al. |
| 6,969,383 B2 | 11/2005 | Hildebrand |
| 7,011,647 B2 | 3/2006 | Purdy et al. |
| 7,025,742 B2 | 4/2006 | Rubenstein et al. |
| 7,108,680 B2 | 9/2006 | Rohr et al. |
| 7,118,549 B2 | 10/2006 | Chan |
| 7,150,737 B2 | 12/2006 | Purdy et al. |
| 7,181,289 B2 | 2/2007 | Pflueger et al. |
| 7,189,221 B2 | 3/2007 | Silverberg et al. |
| 7,214,211 B2 | 5/2007 | Woehr et al. |
| 7,252,659 B2 | 8/2007 | Shehada et al. |
| 7,318,834 B2 | 1/2008 | Njemanze |
| 7,455,666 B2 | 11/2008 | Purdy |
| 7,708,716 B2 | 5/2010 | Shah |
| 7,787,954 B2 | 8/2010 | Purdy |
| 7,842,002 B2 | 11/2010 | Mantle |
| 7,850,723 B1 | 12/2010 | Magers |
| 7,887,503 B2 | 2/2011 | Geiger |
| 8,029,495 B2 | 10/2011 | Pyles |
| 8,131,353 B2 | 3/2012 | Purdy |
| 8,137,334 B2 | 3/2012 | Heruth et al. |
| 8,231,586 B2 | 7/2012 | Kizer et al. |
| 8,357,296 B2 | 1/2013 | Bonhomme et al. |
| 8,398,581 B2 | 3/2013 | Panotopoulos |
| 8,435,204 B2 | 5/2013 | Lad et al. |
| 8,444,661 B2 | 5/2013 | Nair et al. |
| 8,475,419 B2 | 7/2013 | Eckermann |
| 8,486,023 B2 | 7/2013 | Pyles |
| 8,486,104 B2 | 7/2013 | Samson et al. |
| 8,512,280 B2 | 8/2013 | Rozenberg et al. |
| 8,518,636 B2 | 8/2013 | Bosch et al. |
| 8,523,930 B2 | 9/2013 | Saunders et al. |
| 8,603,057 B2 | 12/2013 | Hoffman et al. |
| 8,669,044 B2 | 3/2014 | Chiu et al. |
| 8,679,751 B2 | 3/2014 | Huang |
| 8,721,642 B1 | 5/2014 | Sullivan |
| 8,905,968 B2 | 12/2014 | Thomas |
| 9,205,184 B2 | 12/2015 | Eckermann |
| 9,211,163 B1 | 12/2015 | Jaramaz et al. |
| 9,387,311 B1 | 7/2016 | Heilman et al. |
| 2002/0123714 A1 | 9/2002 | Saul et al. |
| 2002/0156482 A1 | 10/2002 | Scribner et al. |
| 2002/0193285 A1 | 12/2002 | Hesson et al. |
| 2003/0004495 A1 | 1/2003 | Saul |
| 2003/0014016 A1 | 1/2003 | Purdy |
| 2003/0028137 A1 | 2/2003 | Levin |
| 2003/0032915 A1 | 2/2003 | Saul |
| 2003/0065309 A1 | 4/2003 | Barnitz |
| 2003/0072761 A1 | 4/2003 | LeBowitz |
| 2003/0083698 A1 | 5/2003 | Whitehurst et al. |
| 2003/0097082 A1 | 5/2003 | Purdy et al. |
| 2003/0129134 A1 | 7/2003 | Chenard et al. |
| 2003/0130577 A1 | 7/2003 | Purdy et al. |
| 2003/0135196 A1 | 7/2003 | Hesson et al. |
| 2003/0163181 A1 | 8/2003 | Frazer et al. |
| 2003/0199802 A1 | 10/2003 | Barbut |
| 2003/0216687 A1 * | 11/2003 | Hwang ................ A61M 5/3275 604/110 |
| 2004/0015133 A1 | 1/2004 | Karim |
| 2004/0030279 A1 | 2/2004 | Rubenstein et al. |
| 2004/0068221 A1 | 4/2004 | Silverberg et al. |
| 2004/0138125 A1 | 7/2004 | Wang |
| 2004/0138728 A1 | 7/2004 | Wong et al. |
| 2004/0142906 A1 | 7/2004 | Wang |
| 2004/0210231 A1 | 10/2004 | Boucher et al. |
| 2004/0215162 A1 | 10/2004 | Putz |
| 2004/0220545 A1 | 11/2004 | Heruth et al. |
| 2005/0004504 A1 | 1/2005 | Frye et al. |
| 2005/0060006 A1 | 3/2005 | Pflueger et al. |
| 2005/0090801 A1 | 4/2005 | Racz et al. |
| 2005/0149097 A1 * | 7/2005 | Regnell ............. A61M 25/0068 606/191 |
| 2006/0015160 A1 | 1/2006 | Larnard |
| 2006/0030027 A1 | 2/2006 | Ellson et al. |

(56) References Cited

U.S. PATENT DOCUMENTS

| | | |
|---|---|---|
| 2006/0058836 A1 | 3/2006 | Bose et al. |
| 2006/0116605 A1* | 6/2006 | Nakao ............... A61B 10/0266 600/566 |
| 2006/0142783 A1 | 6/2006 | Lewis et al. |
| 2006/0175543 A1 | 8/2006 | Elefteriades |
| 2006/0184098 A1 | 8/2006 | Barnitz |
| 2006/0224101 A1 | 10/2006 | Glenn |
| 2006/0282043 A1 | 12/2006 | Pyles |
| 2007/0050002 A1 | 3/2007 | Elefteriades |
| 2007/0246406 A1 | 10/2007 | Dibel et al. |
| 2008/0045883 A1 | 2/2008 | Radojicic |
| 2008/0154181 A1 | 6/2008 | Khanna |
| 2008/0171990 A1 | 7/2008 | Zauner |
| 2008/0249458 A1 | 10/2008 | Yamasaki |
| 2008/0249501 A1 | 10/2008 | Yamasaki |
| 2008/0319376 A1 | 12/2008 | Wilcox et al. |
| 2009/0076357 A1 | 3/2009 | Purdy |
| 2009/0082800 A1 | 3/2009 | Janardhan |
| 2009/0171369 A1 | 7/2009 | Gayzik |
| 2009/0277850 A1 | 11/2009 | Adams et al. |
| 2010/0030196 A1 | 2/2010 | Hildebrand et al. |
| 2010/0145267 A1 | 6/2010 | Bishop et al. |
| 2010/0168665 A1 | 7/2010 | Skerven |
| 2010/0179509 A1 | 7/2010 | Pyles |
| 2010/0198195 A1 | 8/2010 | Nishtala et al. |
| 2010/0204672 A1 | 8/2010 | Lockhart et al. |
| 2010/0260815 A1 | 10/2010 | Kyle et al. |
| 2010/0280438 A1 | 11/2010 | Thomas |
| 2010/0305492 A1 | 12/2010 | Lad et al. |
| 2010/0324397 A1 | 12/2010 | Purdy |
| 2011/0029050 A1 | 2/2011 | Elefteriades et al. |
| 2011/0046547 A1 | 2/2011 | Mantle |
| 2011/0190831 A1 | 8/2011 | Mafi et al. |
| 2011/0319824 A1 | 12/2011 | Pyles |
| 2012/0004625 A1 | 1/2012 | Velez-Rivera |
| 2012/0149021 A1 | 6/2012 | Yung et al. |
| 2012/0165757 A1 | 6/2012 | Purdy |
| 2012/0203142 A1 | 8/2012 | Bedell |
| 2012/0203290 A1 | 8/2012 | Warren et al. |
| 2012/0209367 A1 | 8/2012 | Prindle et al. |
| 2012/0253266 A1 | 10/2012 | Qureshi et al. |
| 2012/0302938 A1 | 11/2012 | Browd et al. |
| 2012/0330196 A1 | 12/2012 | Nita |
| 2013/0023814 A1 | 1/2013 | Bertrand et al. |
| 2013/0030411 A1 | 1/2013 | Kreck et al. |
| 2013/0035628 A1 | 2/2013 | Garrison et al. |
| 2013/0066331 A1 | 3/2013 | Chitre et al. |
| 2013/0085413 A1 | 4/2013 | Tsamir et al. |
| 2013/0131811 A1 | 5/2013 | Barreiro et al. |
| 2013/0158470 A1 | 6/2013 | Panotopoulos |
| 2013/0158564 A1 | 6/2013 | Harries et al. |
| 2013/0165903 A1 | 6/2013 | Webler et al. |
| 2013/0197422 A1 | 8/2013 | Browd et al. |
| 2013/0248450 A1 | 9/2013 | Kenley et al. |
| 2014/0066830 A1 | 3/2014 | Lad et al. |
| 2014/0166555 A1 | 6/2014 | Dibel et al. |
| 2014/0194840 A1 | 7/2014 | Eckermann |
| 2014/0276334 A1 | 9/2014 | Eckermann |
| 2014/0276660 A1 | 9/2014 | Eckermann |
| 2014/0316373 A1 | 10/2014 | Dhall |
| 2014/0323857 A1 | 10/2014 | Mourad et al. |
| 2014/0378757 A1* | 12/2014 | Allen .................... A61F 2/0045 600/37 |
| 2015/0196742 A1 | 7/2015 | Browd et al. |
| 2015/0223832 A1 | 8/2015 | Swaney et al. |
| 2015/0224284 A1 | 8/2015 | Panotopoulos et al. |
| 2015/0238685 A1 | 8/2015 | Elias et al. |
| 2015/0257774 A1 | 9/2015 | Galdonik et al. |
| 2016/0051801 A1 | 2/2016 | Vase |
| 2016/0101270 A1 | 4/2016 | Browd et al. |
| 2016/0136398 A1 | 5/2016 | Heilman et al. |
| 2016/0174995 A1 | 6/2016 | Turjman et al. |
| 2016/0303355 A1 | 10/2016 | Heilman et al. |
| 2016/0303356 A1 | 10/2016 | Heilman et al. |
| 2017/0000361 A1 | 1/2017 | Meyering et al. |

FOREIGN PATENT DOCUMENTS

| | | |
|---|---|---|
| CA | 2793672 A1 | 9/2011 |
| CA | 2936349 A1 | 7/2015 |
| CN | 101288783 A | 10/2008 |
| CN | 101653637 A | 2/2010 |
| CN | 202409608 U | 9/2012 |
| CN | 102973305 A | 3/2013 |
| CN | 203816046 U | 9/2014 |
| CN | 203935243 U | 11/2014 |
| CN | 105361923 A | 3/2016 |
| EP | 515007 B1 | 12/1996 |
| EP | 1331019 A2 | 7/2003 |
| EP | 2217315 B1 | 5/2012 |
| EP | 2695633 A1 | 2/2014 |
| EP | 2882483 B1 | 9/2016 |
| GB | 2365344 A | 2/2002 |
| JP | 03504681 A | 10/1991 |
| JP | 2001509712 A | 7/2001 |
| JP | 2001513349 A | 9/2001 |
| JP | 2002514096 A | 5/2002 |
| JP | 2003515394 A | 5/2003 |
| JP | 2003250881 A | 9/2003 |
| JP | 2003526398 | 9/2003 |
| JP | 2003526398 A | 9/2003 |
| JP | 2004508109 A | 3/2004 |
| JP | 2004236792 A | 8/2004 |
| JP | 2004528062 A | 9/2004 |
| JP | 2006525827 A | 11/2006 |
| RU | 2100965 C1 | 1/1998 |
| RU | 2158613 C2 | 11/2000 |
| RU | 2290974 C1 | 1/2007 |
| RU | 2312678 C1 | 12/2007 |
| RU | 2314838 C2 | 1/2008 |
| WO | 8909629 A1 | 10/1989 |
| WO | 9205864 | 4/1992 |
| WO | 9802202 | 1/1998 |
| WO | 9833535 A1 | 8/1998 |
| WO | 9907276 A1 | 2/1999 |
| WO | 0041762 | 7/2000 |
| WO | 0043056 | 7/2000 |
| WO | 0051669 A1 | 9/2000 |
| WO | 0139819 A2 | 6/2001 |
| WO | 0154766 A1 | 8/2001 |
| WO | 0211703 A1 | 2/2002 |
| WO | 0220083 A2 | 3/2002 |
| WO | 0232494 A2 | 4/2002 |
| WO | 03015710 A2 | 2/2003 |
| WO | 03020208 A2 | 3/2003 |
| WO | 03057306 A1 | 7/2003 |
| WO | 2004060463 A1 | 7/2004 |
| WO | 2004072647 A1 | 8/2004 |
| WO | 2004093945 A1 | 11/2004 |
| WO | 2004105839 A1 | 12/2004 |
| WO | 2005035025 A1 | 4/2005 |
| WO | 2005044335 A2 | 5/2005 |
| WO | 2005044847 A1 | 5/2005 |
| WO | 2006017763 A2 | 2/2006 |
| WO | 2006079007 A2 | 7/2006 |
| WO | 2006086195 A2 | 8/2006 |
| WO | 2007013945 A2 | 2/2007 |
| WO | 2007110643 A1 | 10/2007 |
| WO | 2008105959 A2 | 9/2008 |
| WO | 2009140202 A1 | 11/2009 |
| WO | 2009155614 A2 | 12/2009 |
| WO | 2010014447 A3 | 2/2010 |
| WO | 2010123558 A1 | 10/2010 |
| WO | 2010127071 A1 | 11/2010 |
| WO | 2011060317 A2 | 5/2011 |
| WO | 2011114260 A1 | 9/2011 |
| WO | 2011150323 A2 | 12/2011 |
| WO | 2012099984 A1 | 7/2012 |
| WO | 2013034602 A1 | 3/2013 |
| WO | 2013052951 A2 | 4/2013 |
| WO | 2014023551 A1 | 2/2014 |
| WO | 2014023552 A1 | 2/2014 |
| WO | 2014039780 A1 | 3/2014 |
| WO | 2014160481 A1 | 10/2014 |
| WO | 2015104631 A1 | 7/2015 |

(56) References Cited

FOREIGN PATENT DOCUMENTS

| WO | 2015109260 A1 | 7/2015 |
|---|---|---|
| WO | 2015157320 A1 | 10/2015 |
| WO | 2016007553 A1 | 1/2016 |

OTHER PUBLICATIONS

International Search Report and Written Opinion of the International Searching Authority for International Patent Application No. PCT/US2016/036626, dated Sep. 8, 2016 (12 pages).
Japanese Rejection of Appeal for related Japanese patent application No. 2009-531646, dated Jan. 25, 2016 (13 pages).
European Search Report and Opinion for European Patent Application No. 07873762.4, dated May 27, 2011 (11 pages).
International Search Report and Written Opinion of the International Searching Authority for International Patent Application No. PCT/US2010/01186, dated Jun. 21, 2010 (7 pages).
International Search Report and Written Opinion of the International Searching Authority for International Patent Application No. PCT/US2007/80834, dated Oct. 28, 2008 (8 pages).
Arnold et al., "Electro-Rotation: Development of a Technique for Dielectric Measurements on Individual Cells and Particles," Journal of Electrostatics, 1988, pp. 151-191, vol. 21.
Arvin et al., "The Role of Inflammation and Cytokines in Brain Injury," Neuroscience and Biobehavioral Reviews, 1996, pp. 445-452, vol. 20, No. 3.
Banci et al., "Metal-free superoxide dismutase forms soluble oligomers under physiological conditions: A possible general mechanism for familial ALS," PNAS, Jul. 3, 2007, pp. 11263-11267, vol. 104, No. 27.
Bayer et al., "Evaluation of the safety and immunogenicity of synthetic Aβ42 (AN1792) in patients with AD," Neurology, Jan. 2005, pp. 94-101, vol. 64.
Becker et al., "Separation of Human Breast Cancer Cells from Blood by Differential Dielectric Affinity," Proc. Natl. Acad. Sci, Jan. 1995, pp. 860-864, vol. 92.
Becker et al., "The Removal of Human Leukaemia Cells for Blood Using Interdigitated Microelectrodes," J. Phys. D: Appl. Phys., 1994, pp. 2659-2662, vol. 27.
Blennow et al., "Alzheimer's disease," Lancet, Jul. 29, 2006, pp. 387-403, vol. 368.
Buzzigoli et al., "Plasmapheresis treatment in Guillain-Barré syndrome: potential benefit over intravenous immunoglobulin," Anaesth Intensive Care, Mar. 2010, pp. 387-389, vol. 38, No. 2, Abstract (1 page).
Cambria et al., "Clinical Experience with Epidural Cooling for Spinal Cord Protection during Thoracic and Thoracoabdominal Aneurysm Repair," Journal of Vascular Surgery, Feb. 1997, pp. 234-243, vol. 25, No. 2.
Caughey et al., "Protofibrils, pores, fibrils, and neurodegeneration: separating the responsible protein aggregates from the innocent bystanders*," Annu. Rev. Neurosci., 2003, pp. 267-298, vol. 26.
Cook, "Combined Spinal-Epidural Techniques," Anaesthesia, 2000, pp. 42-64, vol. 55.
Covaciu et al., "Brain Temperature in Volunteers Subjected to Intranasal Cooling," Intensive Care Med., Aug. 2011, pp. 1277-1284, vol. 37, No. 8, Abstract (1 page).
Dawson et al., "Molecular Pathways of Neurodegeneration in Parkinson's Disease," Science, Oct. 21, 2003, pp. 819-822, vol. 302.
Dekosky et al., "Looking Backward to Move Forward: Early Detection of Neurodegenerative Disorders," Science, Oct. 31, 2003, pp. 830-834, vol. 302.
Delhaas, "Extradural and Subarachnoid Catheterization Using the Seldinger Technique," British Journal of Anaesthesia, 1996, pp. 149-150, vol. 76.
Dias-Santagata et al., "Oxidative stress mediates tau-induced neurodegeneration in *Drosophila*," Journal of Clinical Investigation, Jan. 2007, pp. 236-245, vol. 117.

Dunnett et al., "Prospects for new restorative and neuroprotective treatments in Parkinson's disease", Nature, Jun. 24, 1999, pp. A32-A38, SUPP, vol. 399.
Elefteriades et al., "Litigation in Nontraumatic Aortic Diseases—A Tempest in the Malpractice Maelstrom," Cardiology, 2008, pp. 263-272, vol. 109.
Enchev et al., "Historical Trends of Neuroendoscopic Surgical Techniques in the Treatement of Hydrocephalus," Neurosurgery Review, 2008, pp. 249-262, vol. 31.
Gascoyne et al., "Dielectrophoretic Separation of Cancer Cells from Blood," IEEE Transactions of Industry Applications, May/Jun. 1997, pp. 670-678, vol. 33, No. 3.
Gascoyne et al., "Isolation of Rare Cells from Cell Mixtures by Dielectrophoresis," Electrophoresis, Apr. 2009, pp. 1388-1398, vol. 30, No. 8.
Gascoyne et al., "Particle Separation by Dielectrophoresis," Electrophoresis, Jul. 2002, pp. 1973-1983, vol. 23, No. 13.
Gilman et al., "Clinical effects of Aβ immunization (AN1792) in patients with AD in an interrupted trial," Neurology, May 2005, p. 1553-1562, vol. 64.
Glabe, "Common mechanisms of amyloid oligomer pathogenesis in degenerative disease," Neurobiology of Aging, 2006, pp. 570-575, vol. 27.
Haltiwanger, "The Electrical Properties of Cancer Cells," www.royalrife.com/haltiwanger1 (62 pages).
Han et al., "An Electrorotation Technique for Measuring the Dielectric Properties of Cells with Simultaneous Use of Negative Quadropolar Dielectrophoresis and Electrorotation," The Royal Society of Chemisty, Analyst, 2013, pp. 1529-1537, vol. 138.
Hansson et al., "Association between CSF biomarkers and incipient Alzheimer's disease in patients with mild cognitive impairment: a follow-up study," Lancet Neurol., Mar. 2006; pp. 228-234, vol. 5.
Helmy et al., "The Cytokine Response to Human Traumatic Brain Injury: Temporal Profiles and Evidence for Cerebral Parenchymal Production," Journal of Cerebral Blood Flow & Metabolism, 2011, pp. 658-670, vol. 31.
Hock et al., "Antibodies against beta-amyloid slow cognitive decline in Alzheimer's disease," Neuron, May 22, 2003, pp. 547-554, vol. 38.
Hohlfeld et al., "Autoimmune concepts of multiple sclerosis as a basis for selective immunotherapy: From pipe dreams to (therapeutic) pipelines," PNAS, Oct. 5, 2004, pp. 14599-14606, vol. 101, Suppl. 2.
Huang et al., "Electrode Design for Negative Dielectrophoresis," Measurement Science and Technology, Dec. 1991, pp. 1142-1146, vol. 2.
Janus et al., "A beta peptide immunization reduces behavioural impairment and plaques in a model of Alzheimer's disease," Nature, Dec. 2000, pp. 979-982, vol. 408.
Jones et al., "Multipolar Dielectrophoretic and Electrorotation Theory," Journal of Electrostatics, 1996, pp. 121-134, vol. 37.
Kessler et al., "Endothelin-1 levels in plasma and cerebrospinal fluid of patients with cerebral vasospasm after aneurysmal subarachnoid hemorrhage," Surgical Neurology, 2005, pp. S1:2-S1:5, vol. 64.
Koo et al., "Amyloid diseases: Abnormal protein aggregation in neurodegeneration," Proc. Natl. Acad. Sci., Aug. 1999, pp. 9989-9990, vol. 96.
Kuwabara et al., "Intravenous immunoglobulin therapy for Guillain-Barré syndrome with IgG anti-GM1 antibody," Muscle & Nerve, Jan. 2001, pp. 53-58.
Lau et al., "Tau Protein Phosphorylation as a Therapeutic Target in Alzheimer's Disease," Current Topics in Medicinal Chemistry, 2002, pp. 395-415, vol. 2.
Levi et al., "Clinical Application of Modest Hypothermia After Spinal Cord Injury," J. Neurotrauma, Mar. 2009, pp. 407-415, vol. 26, No. 3, Abstract (1 page).
Li et al., "Continuous Dielectrophoretic Cell Separation Microfluidic Device," The Royal Society of Chemistry, Lab Chip, 2007, pp. 239-248, vol. 7.
MacDonald et al., "Cerebral vasospasm after subarachnoid hemorrhage: the emerging revolution," Nature Clinical Practice, Neurology, May 2007, pp. 256-263, vol. 3, No. 5.

(56) References Cited

OTHER PUBLICATIONS

Madeira-Lopes et al., "Comparative Study of the Temperature Profiles of Growth and Death of the Pathogenic Yeast *Cryptococcus Neoformans* and the non-pathogenic *Cryptococcus Albidus*," Journal of Basic Microbiology, 1986, pp. 43-47, vol. 26.
Markx et al., "Dielectrophoretic Separation of Bacteria Using a Conductivity Gradient," Journal of Biotechnology, Dec. 1996, pp. 175-180, vol. 51.
Markx et al., "Dielectrophoretic Separation of Cells: Continuous Separation," Biotechnology and Bioengineering, Feb. 1995, pp. 337-343, vol. 45, No. 4.
Marszalek et al., "Determination of Electric Parameters of Cell Membranes by a Dielectrophoresis Method," Biophysical Journal, May 1991, pp. 982-987, vol. 59.
Mascia et al., "Temporal Relationship Between Endothelin-1 Concentrations and Cerebral Vasospasm in Patients With Aneurysmal Subarachnoid Hemorrhage—Editorial Comment: Endothelin-1 in Vasospasm After SAH," Stroke, May 2001, pp. 1185-1190.
McCulloch et al., "A radical approach to stroke therapy," PNAS, Sep. 25, 2001, pp. 10989-10991, vol. 98, No. 20.
Mckeating et al., "Cytokines and Adhesion Molecules in Acute Brain Injury," British Journal of Anaesthesia, 1998, pp. 77-84, vol. 80.
MckHann et al., "Plasmapheresis and Guillain-Barré syndrome: analysis of prognostic factors and the effect of plasmapheresiss," Annals of Neurology, Apr. 1988, pp. 347-353, vol. 23, No. 4.
Melnikova, "Therapies for Alzheimer's disease", "Therapies for Alzheimer's disease," Nature Reviews, May 2007, pp. 341-342, vol. 6.
Misaki et al., "Contrast-Enhanced Fluid-Attenuated Inversion Recovery MRI Is Useful to Detect the CSF Dissemination of Glioblastoma," Journal of Computer Assisted Tomography, 2001, pp. 953-956, vol. 25, No. 6.
Monsonego et al., "Immunotherapeutic Approches to Alzheimer's Disease", "Immunotherapeutic Approches to Alzheimer's Disease," Science, Oct. 31, 2003, pp. 834-838, vol. 302.
Morgan et al., "A beta peptide vaccination prevents memory loss in an animal model of Alzheimer's disease," Nature, Dec. 2000, pp. 982-985, vol. 408.
Morganti-Kossman et al., "Production of Cytokines Following Brain Injury: Beneficial and Deleterious for the Damaged Tissue," Molecular Psychiatry, 1997, pp. 133-136, vol. 2.
Nicoll et al., "Abeta species removal after abeta42 immunization," Journal of Neuropathology Exp. Neurol., Nov. 2006, pp. 1040-1048, vol. 65, No. 11.
Noseworthy, "Progress in determining the causes and treatment of multiple sclerosis," Nature, Jun. 24, 1999, pp. A40-A47, vol. 399, Supp.
Onda et al., "Cerebral Glioblastoma with Cerebrospinal Fluid Dissemination: A Clinicopathological Study of 14 Cases Examined by Complete Autopsy," Neurosurgery, 1989, pp. 533-540, vol. 25, No. 4.
Orgogozo et al., "Subacute meningoencephalitis in a subset of patients with AD after Aβ42 immunization," Neurology, Jul. 2003, pp. 46-54, vol. 61.
Park et al., "3-D Electrode Designs for Flow-Through Dielectrophoretic Systems," Electrophoresis, 2005, pp. 3745-3757, vol. 26.
Parkhill et al., "The genome sequence of the food-borne pathogen Campylobacter jejuni reveals hypervariable sequences," Nature, Feb. 10, 2000, pp. 665-668, vol. 403.
Perfect, "*Cryptococcus Neoformans:* The Yeast that Likes it Hot," FEMS Yeast Res., 2006, pp. 463-468, vol. 6.
Pethig et al., "Applicants of Dielectrophoresis in Biotechnology," Tibtech, Oct. 1997, pp. 426-432, vol. 15.
Pethig, "Dielectrophoresis: Status of the Theory, Technology, and Applications," Biomicrofluidics, 2010, pp. 022811-1-02281-35, vol. 4.
Pethig, "Dielectrophoresis: Using Inhomogeneous AC Electrical Fields to Separate and Manipulate Cells," Critical Reviews in Biotechnology, 1996, pp. 331-348, vol. 16, No. 4.

Polderman et al., "Therapeutic Hypothermia and Controlled Normothermia in the Intensive Care Unit: Practical Considerations, Side Effects, and Cooling Methods," Crit. Care Med., Mar. 2009, pp. 1101-1120, vol. 37, No. 3, Abstract (1 page).
Reiber, "Proteins in cerebrospinal fluid and blood: Barriers, CSF flow rate and source-related dynamics", REIBER, Restorative Neurology and Neuroscience, 2003, pp. 79-96, vol. 21.
Roberson et al., "100 Years and Counting: Prospects for Defeating Alzheimer's Disease," Science, Nov. 3, 2006, pp. 781-784, vol. 314.
Rowland, "Amyotrophic Lateral Sclerosis: Human Challenge for Neuroscience," Proc. Natl. Acad. Sci., Feb. 1995, pp. 1251-1253, vol. 92.
Shoulson, "Experimental Therapeutics of Neurodegenerative Disorders: Unmet Needs," Science, Nov. 6, 1998, pp. 1072-1074, vol. 282.
Steece-Collier et al., "Etiology of Parkinson's disease: Genetics and environment revisited," PNAS, Oct. 29, 2002, pp. 13972-13974, vol. 99, No. 22.
Stephens et al., "The Dielectrophoresis Enrichment of CD34 Cells from Peripheral Blood Stem Cell Harvests," Bone Marrow Transplantation, 1996, pp. 777-782, vol. 18.
Tay et al., "Electrical and Thermal Characterization of a Dielectrophoretic Chip with 3D Electrodes for Cells Manipulation," Electrochimica. Acta., 2007, pp. 2862-2868, vol. 52.
Taylor et al., "Toxic Proteins in Neurodegenerative Disease", "Toxic Proteins in Neurodegenerative Disease," Science, Jun. 14, 2002, pp. 1991-1995, vol. 296.
Author Unknown, "External CSF Drainage," Aqueduct Neurosciences, Jul. 2014 (2 pages).
Author Unknown, "Therapeutic Hypothermia for Spinal Cord Injury," Crit. Care Med., Jul. 2009, pp. S238-S242, vol. 37, Supp. 7, Abstract (1 page).
Author Unknown, LiquoGuard, Moller Medical, Brochure (2 pages).
Author Unknown, World Journal of Radiology, Jun. 28, 2012, pp. 241-290, vol. 4, No. 6.
Valentine et al., "Misfolded CuZnSOD and amyotrophic lateral sclerosis," PNAS, Apr. 1, 2003, pp. 3617-3622, vol. 100, No. 7.
Vernino et al., "Autoimmune encephalopathies," The Neurologist, May 2007, pp. 140-147, Bol. 13, No. 3.
Voldman, "Electrical Forces for Microscale Cell Manipulation," Annu. Rev. Biomed. Eng., 2006, pp. 425-454, vol. 8.
Weis et al., "Noninvasive Monitoring of Brain Temperature During Mild Hypothermia," Magn. Reson. Imaging, Sep. 2009, pp. 923-932, vol. 27, No. 7, Abstract (1 page).
Wollinsky et al., "CSF filtration is an effective treatment of Guillain-Barré syndrome: A randomized clinical trial," Neurology, Sep. 2001, pp. 774-780, vol. 57.
Yuki et al., "Carbohydrate mimicry between human ganglioside GM1 and Campylobacter Jejuni lipooligosaccharide causes Guillain-Barré syndrome," PNAS, Aug. 3, 2004, pp. 11404-11409, vol. 101, No. 31.
Ziebell et al., "Involvement of Pro- and Anti-Inflammatory Cytokines and Chemokines in the Pathophysiology of Traumatic Brain Injury," Neurotherapeutics: The Journal of the American Society for Experimental. NeuroTherapeutics, Jan. 2010, pp. 22-30, vol. 7.
European Office Action for European Patent Application No. 07873762.4, dated Dec. 7, 2016 (5 pages).
Mahon et al., "North American Clinical Experience with the EKOS MicroLysUS Infusion Catheter for the Treatment of Embolic Stroke," AJNR Am J. Neuroradiology, Mar. 2003, pp. 534-538, vol. 24.
Rogers et al., "Percutaneous aspiration of brain tumor cysts via the Ommaya reservoir system," Neurology, Feb. 1991, pp. 279-282, vol. 41.
Siddiqui et al., "Use of the Penumbra System 054 plus Low Dose Thrombolytic Infusion for Multifocal Venous Sinus Thrombosis," Interventional Neuroradiology, 2012, pp. 314-319, vol. 18.
Spiegelberg GmbH & Co. KG, "EVD—Catheters," downloaded on Nov. 3, 2016 from website, http://www.spiegelberg.de/products/drainage/silverline_evd_catheter_3001002.html (1 page).
Wagner et al., "Ultra-early clot aspiration after lysis with tissue plasminogen activator in a porcine model of intracerebral hemorrhage: edema reduction and blood-brain barrier protection," J. Neurosurg., Mar. 1999, pp. 491-498, vol. 90.

(56) References Cited

OTHER PUBLICATIONS

Ziu et al., "A Series of Cerebral Venous Sinus Thromboses Treated with Intra-Arterial tPA infused over Ten Hours with a 0.027-inch Catheter and Literature Review," Jun. 23, 2016, pp. 1-13.
Hedstrom et al., U.S. Appl. No. 15/367,592, filed Dec. 2, 2016.
Meyering et al., U.S. Appl. No. 15/229,392, filed Aug. 5, 2016.
Meyering et al., U.S. Appl. No. 15/177,638, filed Jun. 6, 2016.
Vase et al., U.S. Appl. No. 15/287,174, filed Oct. 6, 2016.

* cited by examiner

INTRODUCER SHEATH AND PUNCTURE TOOL FOR THE INTRODUCTION AND PLACEMENT OF A CATHETER IN TISSUE

CROSS-REFERENCE TO RELATED APPLICATIONS

This application claims the benefit under 35 U.S.C. § 119 of the earlier filing date of U.S. Provisional Application No. 62/187,460, filed Jul. 1, 2015, entitled "Introducer Sheath and Puncture Tool for the Introduction and Placement of a Catheter in Tissue," which is hereby incorporated by reference in its entirety as if fully set forth herein for any and all purposes.

BACKGROUND

Some medical procedures, such as percutaneous procedures, involve the introduction and placement of a catheter into a human or animal subject. Commonly, a puncture into the subject is created, followed by the introduction of a sheath after the needle or tool has been removed. Multiple introductions of tools into a wound space can increase bleeding, move tissue, and cause tissue damage. In addition, the catheter may require repositioning during therapy. Repositioning a catheter may increase a risk of introducing contaminants. In addition, currently, multi-lumen catheters cannot be delivered through a straight needle or Tuohy needle because the catheter hub cannot be removed. There is a need in the art for an improved puncture tool.

SUMMARY

Certain embodiments of a medical device may comprise a handle, a needle, a sheath, and a barrier. A proximal end of the needle may be releasably connected to a distal end of the handle by a fastener. The sheath may be disposed around the needle and a proximal end of the sheath may be releasably connected to the distal end of the handle by the fastener. The barrier may be disposed around the sheath and the needle and have a proximal zone and a distal zone connected by a covering.

In certain implementations, the fastener may comprise a Luer fitting or a 3-way stopcock. The needle may comprise an angled tip. The angle of the tip may be between 5 and 10 degrees. The handle may further comprise a port in fluid connection with an inner lumen of the sheath. The sheath may be braided. The handle may further comprise a button or releasing the needle. The handle may be egg shaped.

Certain embodiments may include a method for performing a procedure at a surgical site of a human or animal subject, the method may include receiving a medical device comprising: a handle; a needle releasably connected to the handle; a sheath disposed around the needle and releasably connected to the handle; a barrier disposed around the sheath and the needle, the barrier being in a collapsed configuration and having a proximal zone attached to the proximal end of the sheath and a distal zone connected to the proximal zone by a covering. The method may further include deploying the barrier to an expanded configuration; attaching the distal zone to a tissue near the surgical site; inserting the sheath and the needle into the surgical site at substantially the same time; releasing the needle from the handle; removing the needle from the surgical site; and performing a procedure through the sheath.

In certain implementations, performing the procedure may comprise aspirating or deploying fluid via a 3-way stopcock connected to the sheath. The distal zone may further comprise an adhesive strip and the distal zone may be attached to the tissue using the adhesive strip. The sheath and the needle may be inserted without using a guidewire. Attaching the distal zone to the tissue may facilitate maintenance of an aseptic environment within a space bounded by the barrier, the distal zone, and the proximal zone. The needle may be removed from the surgical site through a port in the handle. The method may further comprise inserting a stylet within a lumen of the needle and collecting data using a sensor disposed on the stylet. Performing the procedure through the sheath may comprise inserting a multi-lumen catheter into the sheath and attaching the catheter to the sheath. The needle may be an atraumatic needle Certain embodiments may include a method for removing a volume of cerebrospinal fluid (CSF) from a subarachnoid space of human or animal subject. The method may include receiving a medical device comprising: a handle comprising a port; a needle releasably. connected to the handle, the needle having a tip curved; an expandable, braided sheath disposed around the needle, the sheath releasably connected to the handle using a Luer fitting, and in fluid connection with the port; and a barrier disposed around the sheath and the needle, the barrier being in a collapsed configuration and having a proximal zone attached to the proximal end of the sheath and a distal zone connected to the proximal zone by a covering. The method may further include expanding the barrier to an expanded configuration; attaching the distal zone to a tissue near the surgical site; inserting the sheath and the needle into the subarachnoid space at substantially the same time; withdrawing the needle from the sheath; and collecting CSF from the subarachnoid space through the port.

In certain implementations, the method may further include attaching a manometer to the port and measuring a pressure within the subarachnoid space using the manometer. The method may further comprise processing the collected CSF and returning the CSF into the subarachnoid space.

DETAILED DESCRIPTION

Disclosed embodiments generally relate to an introducer sheath and puncture tool for the introduction and placement of a catheter into a subject. For example, certain implementations may describe a puncture tool that may simultaneously deliver a sheath and a needle to a desired anatomical location. Additional information is provided in U.S. patent application Ser. No. 14/743,652, entitled "Devices and Systems for Access and Navigation of Cerebrospinal Fluid Space," filed Jun. 18, 2015, which claims the benefit of U.S.

Provisional Patent Application Ser. No. 62/038,998, which are both hereby incorporated by reference for all purposes as if fully set forth herein.

Figure 1:
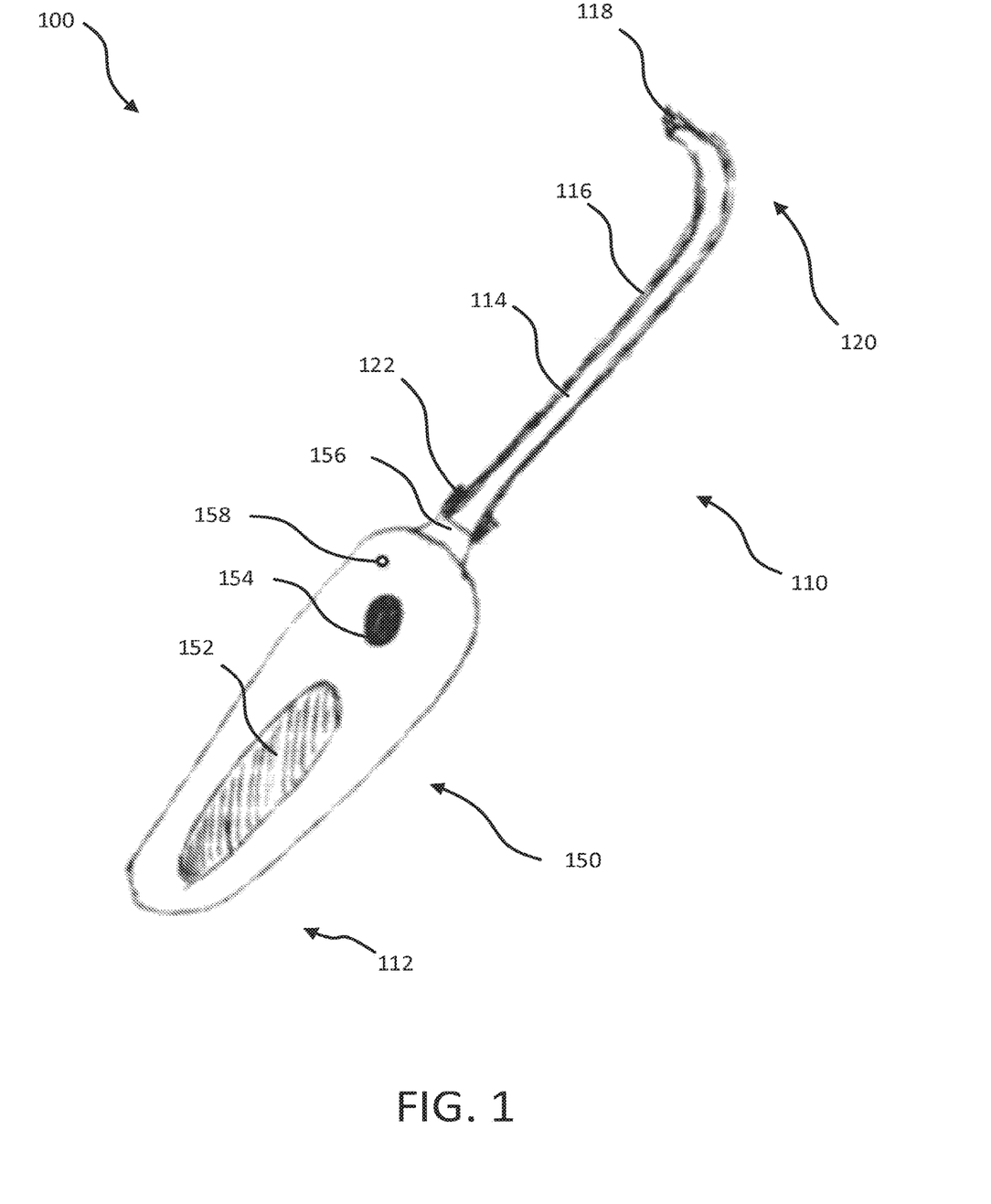
FIG. 1 illustrates a device according to certain implementations.

FIG. 1 illustrates a device 100 having a proximal end 112, a needle 114, a sheath 116, a tip 118, a distal end 120, a fastener 122, and a handle 150. The proximal end 112 describes a portion of the device 100 away from the tip 118 and the distal end 120 describes the end of the device 100 near the tip 118.

Needle 114

In certain implementations, the needle 114 may be an elongate needle defining an inner lumen, including a distal opening and a proximal opening. The needle 114 may be constructed from various materials, including but not limited to stainless steel. The gauge of the needle 114 may be chosen based on the type of procedure in which the needle 114 will be used. For instance, an approximately 18-gauge to approximately 25-gauge needle may be used for lumbar puncture procedures; however, other sizes may also be used. Further, other characteristics of the needle may change depending on the procedure. For instance, an atraumatic needle 114 (e.g., a Tuohy needle, a Whitacre needle, and/or a Sprotte needle) may be used in a lumbar puncture or other procedures. Atraumatic needles may have pencil-point shaped tips. Atraumatic needles may be contrasted from cutting needles (e.g., a Quincke needle), which typically have a tip designed to cut tissue. In certain implementations, the needle 114 may be configured as a solid needle.

Figure 2:
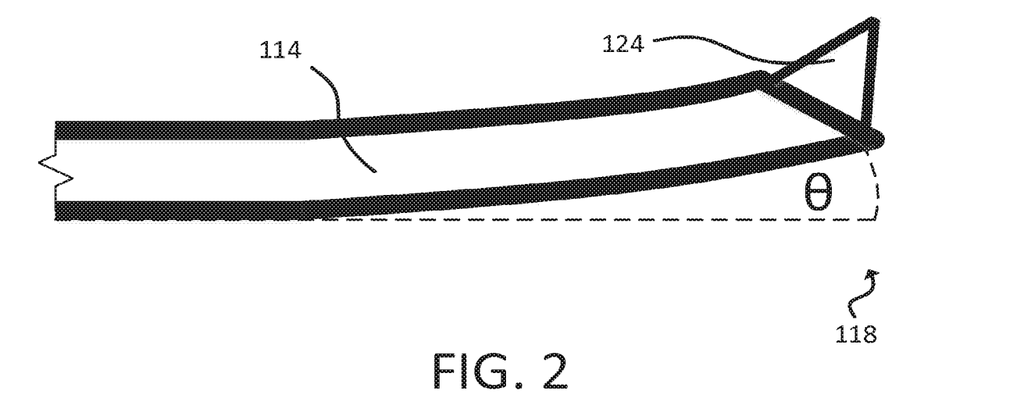
FIG. 2 illustrates a portion of a tip of a needle having an angle according to certain implementations.

FIG. 2 illustrates the tip region 118 of the needle 114 having an angle θ and a stylet 124. In certain embodiments, the tip region 118 of the needle 114 may extend in a direction different from the rest of the needle 114. The angle θ between the tip region 118 and the rest of the needle 114 may be between approximately 5 degrees and approximately 10 degrees towards the top of the handle 150. However, other angles or directions of angles are possible, including tips 118 with no angles or with angles greater than approximately 10 degrees. The length of the portion of the needle 114 that is angled may vary depending on the desired procedure and/or the preferences of the operator. For example, the length may be between approximately 1 mm to approximately 10 mm; however, other configurations are possible. The angled tip 118 may facilitate insertion and navigation of the needle 114 during the procedure.

In certain embodiments, a stylet 124 may be inserted through the needle 114. The stylet 124 may be, for example, an elongate probe. In certain embodiments, the stylet 124 may have a tip that is sharp or otherwise designed to facilitate the insertion of the distal end of the needle 114. The stylet 124 may also include various sensors. For example, the stylet 124 may include a camera, light, and/or other visualization devices, and/or sensors for such devices. These devices and sensors may be used to assist in navigation and proper placement of the device 100, as well as the collection of diagnostic and other information.

Sheath 116

Returning to FIG. 1, the sheath 116 may be an elongate, flexible tube that defines an inner lumen with distal and proximal openings. The sheath 116 may maintain or create a space in or through which a procedure may be conducted. The sheath 116 may be constructed from various materials. In certain implementations, the sheath 116 comprises a polymer layer surrounding a metal layer. For example, the sheath 116 may include a flexible nitinol layer surrounded by a polymer, such as polyurethane. The sheath 116 may be expandable, such that the sheath 116 may transition from a compressed configuration to an expanded configuration having a greater diameter. For example, the sheath 116 may have a compressed diameter of approximately 0.5 mm and an expanded diameter of approximately 1.5 mm. Other diameters may be used, depending on the application. One or more of the layers of the sheath 116 may comprise a braided, woven, or nonwoven material. In certain implementations, the sheath 116 or other components of the device 100 may be constructed to be radiopaque, for example, by compounding radiopaque materials into the polymer or by adding radiopaque bands or components to the tip or body of the sheath. The sheath 116 may also be constructed such that the internal layer is expandable and can conform around various size needles, guidewires, stylets, or catheters that may be placed through the sheath 116 while minimizing fluid leakage. The sheath 116 may also comprise antimicrobial, antibacterial, antifungal, analgesic, or other agents or chemicals.

The properties of the sheath 116 may be selected for use with a particular procedure or in a particular environment. For example, the sheath 116 may comprise hydrophilic regions, or a low-friction material, so as to decrease friction during placement. As another example, the layering or braiding of the sheath 116 may be chosen to increase or decrease the stiffness or thickness of the sheath to make the sheath 116 more suitable for use with particular needles 114. For instance, embodiments with increased flexibility may make the sheath 116 more suitable for use with epidural needles, which may have curved tips or side ports. In addition, the sheath 116 may be configured to be durable enough to withstand a needle or stylet being passed through the sheath 116 and contacting internal surfaces of the sheath 116. The sheath 116 may be constructed such that a sharp metal object traveling through the lumen will not cause delamination of sheath material.

In certain implementations, the sheath 116 may have a larger diameter than the diameter of the needle 114, such that the needle 114 may be disposed within the inner lumen of the sheath 116. In certain other implementations, the sheath 116 may be capable of being inserted through the needle 114. The relationship between the needle 114 and the sheath 116 may be such that the needle 114 and sheath 116 may be substantially simultaneously introduced into tissue. When the needle 114 is placed within the sheath 116, it may fit tight enough to substantially resist fluid leak between the two units. Additionally, the fit of the needle 114 within the sheath 116 (or sheath 116 within the needle 114) may be configured to be tight enough such that the combined unit does not catch on tissue or bone during placement within the body.

Fastener 122

The fastener 122 may enable connections between two or more components. For example, in certain embodiments, the fastener 122 may be attached to the proximal end of the sheath 116 and enable the sheath 116 to be releasably attached to another component, such as the handle 150, the needle 114, and/or another device. The fastener 122 may be of the Luer-lock or Luer-slip variety. In other implementations, other suitable fastening methods may be used. In certain implementations, the distal end of the sheath 116 may be sealable to prevent leakage or entry of materials.

In certain implementations, the fastener 122 may be used with different devices during a single procedure. For example, the sheath 116 may be connected to the handle 150 via the fastener 122 during the insertion of the sheath 116. After insertion, the handle 150 may be disconnected from the sheath and a different device, such as a multi-lumen catheter, 3-way stopcock, or a port, may be inserted into the sheath 116 and/or attached to the sheath 116 via the fastener 122.

Handle 150

In certain implementations, the handle 150 is a portion by which the device 100 may be held or controlled. The handle 150 may include a grip 152, a button 154, a locking mechanism 156, and a port 158. The handle 150 may take various shapes, sizes, and configurations. For example, the handle 150 may be configured to fit within a palm and have an ergonomic shape. Any suitable shape may be used, including a shape that is, for example, similar to that of an egg. The handle 150 may be constructed from various materials, including but not limited to thermoplastic elastomers (such as those sold under the trade name SANTOPRENE). The handle 150 may also comprise springs, expandable material, levers, and other components.

The button 154 may be a user-accessible button on the handle 150 for controlling one or more features of the device 100. For example, the locking mechanism 156 may be operably coupled to the button 154 such that manipulating the button 114 may operate the locking mechanism 156. The button 154 may be constructed from various materials, including but not limited to polycarbonate materials.

The grip 152 may be one or more regions on an exterior surface of the handle 150 for improving the ability to hold the device. For example, the grip 152 may have raised, lowered, bumpy, wavy, knurled, or other kinds of surface features.

The locking mechanism 156 may be a feature of the handle 150 capable of locking or otherwise engaging with another component, for example, the fastener 122, the sheath 116 and/or a fastening portion of the needle 112. The locking mechanism 156 may have features capable of being manipulated to lock, unlock, release, engage, or otherwise operate the locking mechanism 156, including but not limited to threads or other fasteners.

The port 158 may be one or more openings within the handle 150. In certain implementations, the opening of the port 158 may be in fluid connection with the needle 114 and/or the sheath 116 to enable the collection or infusion of fluid, such as cerebrospinal fluid (CSF), or the addition of pharmaceutical or other compounds or materials. Exemplary procedures are discussed in U.S. Pat. No. 8,435,204, which is hereby incorporated by reference for this and other purposes. In certain embodiments, the port 158 may facilitate the removal or introduction of a tool. For example, the needle 114 may be capable of being detached and removed through the port 158. As another example, various tools (such as a catheter, including a multi-lumen catheter) may be introduced through the port 158.

Barrier 160

Figure 3A:
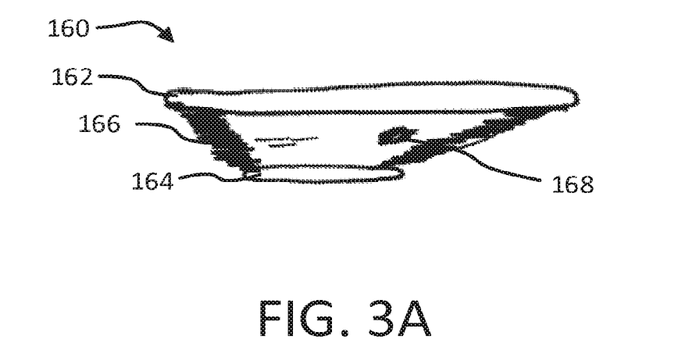
FIG. 3A illustrates a barrier in a collapsed configuration according to certain implementations.
Figure 3B:
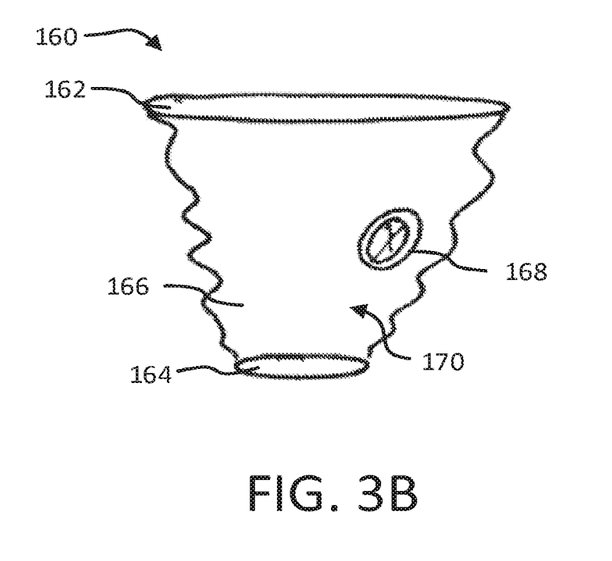
FIG. 3B illustrates a barrier in an expanded configuration according to certain implementations.

FIGS. 3A and 3B illustrate a barrier 160 according to certain implementations, including a distal zone 162, a proximal zone 164, a covering 166, a barrier port 168, and an environment 170. The barrier 160 may be a movable region or combination of regions that may be used to define one or more boundaries of an environment 170. For instance, the barrier 160 may be a collapsible sleeve that is resistant or substantially impermeable to biological and other contaminants. The barrier 160 may be configured to create or maintain aseptic conditions in the environment 170. In certain embodiments the barrier 160 is collapsible or otherwise capable of transitioning from a collapsed configuration to a deployed or extended configuration. For example, the barrier 160 may be extended over the exited portion of an indwelling catheter.

The distal zone 162 may be a collar or region of the barrier 160 that defines a distal opening and may be configured for attachment to a region near a surgical site. The surgical site may be a location of the subject at or through which a procedure may be conducted. The distal zone 162 may have an attachment feature, such as peel-away adhesive strip that may be used to attach the distal zone 162 to a surface (such as skin or other tissue of a subject) to facilitate creation of the environment 170. In certain other embodiments, the attachment feature may be capable of attachment to another device to create a barrier, including a sealed, aseptic barrier. For example, the distal zone 162 may be capable of attaching to an introducer. The introducer may be a device used to create an opening in tissue through which a procedure may be conducted.

The proximal zone 164 may be a collar or region of the barrier 160 that defines a proximal opening and may be configured for attachment to a region near a device. For example, the proximal zone 164 may have an attachment feature such as a peel-away strip, threaded, magnetic, or other connection that may be used to attach the proximal zone 164 to a tool and/or substantially seal the proximal opening. The proximal zone 164 may be releasably, fixedly, or permanently mounted to the device 100.

The covering 166 may be a flexible or collapsible material or sheet connecting the distal zone 162 to the proximal zone 164. The covering 166 may be constructed of various materials that are resistant or substantially impermeable to contaminants. The degree of impermeability may depend on the desired use. For example, the covering 166 may be used to maintain an aseptic environment according to standards within a particular industry. The covering 166 may be constructed from a transparent or semi-transparent material to enable a user to see through the covering 166 to the surgical site. In addition, the material may be thin and flexible, but durable to resist puncture or tearing. Suitable materials may include, but are not limited to, high-density polyethylene and other polymers.

In certain embodiments, the barrier port 168 is an opening in the covering 166 of the barrier 160 that may be used to access the surgical site even when the proximal zone 164 and distal zone 162 are sealed or fixed in place. The port 168 may be an opening through which tools may be used, a window through which the site is visible, a window through which the site is magnified, a connector to which tools or devices may be attached, or an otherwise useful area. For example, in certain implementations, the barrier port 168 may be configured as an injection and/or aspiration port or be configured as a space through which aspiration and/or injections may take place.

In addition, or instead, the barrier port 168 may be a one-way or two-way valve that enables the flow of air or materials between the inside and outside of the barrier 160. This configuration may be useful in situations where the deployment of the barrier 160 creates a substantially airtight seal and the barrier 160 is collapsed or expanded during a procedure. Without a valve, there may be undesired consequences, such as forcing air from inside the environment 170 in the interior of the barrier 160 into the subject or breaching a seal. The valve may include a filter or other means for substantially maintaining the aseptic qualities of the environment despite movement of air. In certain implementations, the valve, filter, or other portions may be treated with an antimicrobial, antibacterial, antifungal, analgesic, a drug that is specific to the procedure (e.g., an agent to potentiate cell growth in a burn patient) or other agents or chemicals.

The shapes, sizes, and dimensions of the barrier 160 and the environment may vary depending on the type of procedure being performed and desired characteristics. The barrier 160 may take various shapes and forms, including but not limited to frustoconical, spherical, or other three-dimensional shapes. A desired shape may be dictated by the type of procedure being performed. For example, the procedure may require placement and relocation of the device 100 over a large region and therefore, a barrier 160 having a large distal zone 162 may be desired.

FIG. 3A illustrates a frustoconical barrier 160 in a substantially collapsed configuration. The collapsed configuration may be a configuration in which the distal zone 162 and the proximal zone 164 are substantially closer together than in an expanded configuration. In certain embodiments, the covering 166 of the barrier 160 may facilitate the creation of the collapsed configuration by having pleats or otherwise being folded rather than being crumped. The covering 166 may be twisted to create the collapsed state. Other configurations and methods for collapsing or otherwise reducing the length of the barrier 160 may be used.

FIG. 3B illustrate the barriers 160 in an expanded or otherwise deployed configuration. This configuration is characterized by the distal zone 162 and the proximal zone 164 being substantially more spatially separated than in the collapsed configuration. The amount of separation may vary depending on the procedure and tools being used. Large tools and/or large tool travel distances may make a larger separation preferable.

Method of Using

Figure 4:
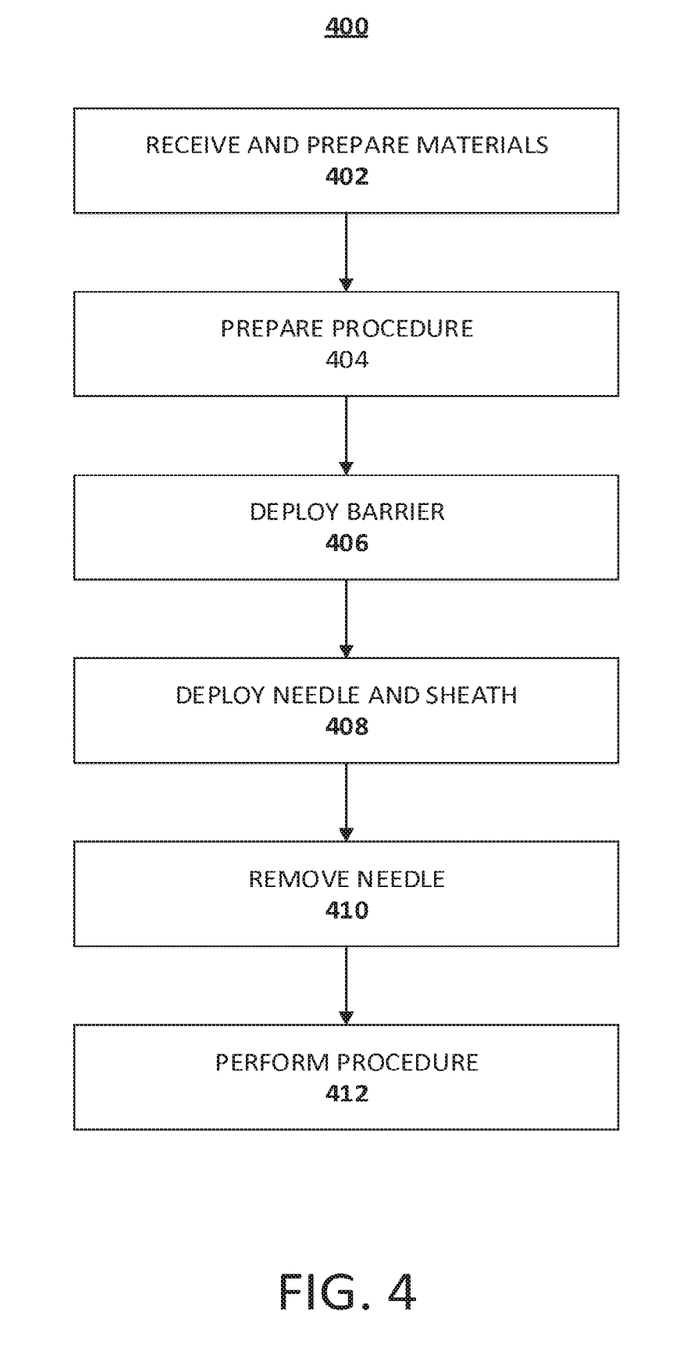
FIG. 4 illustrates a method of using the device according to certain implementations.

FIG. 4 illustrates a method 400 of using the device 100 according to certain implementations, including the steps of receiving and preparing materials 402, preparing the procedure 404, deploying the barrier 406, deploying the needle and sheath 408, removing the needle 410, and performing the procedure 412.

Receiving and Preparing Materials 402

Receiving and preparing materials 402 may include gathering and preparing the materials necessary to perform a particular procedure on a subject. This may include receiving the device 100 in a pre-assembled or partially assembled state. The device 100 and one or more of its components may have been specifically chosen for the particular procedure and the particular patent. For example, a specific handle 150, needle 114, sheath 116, and barrier 160 may be chosen from a collection of parts or a kit. The materials may be stored in individual sterile packaging and are removed prior to assembly.

Once the materials are gathered, the materials may be combined, as needed. For example, a fastener 122 may be used with the locking mechanism 156 to place the sheath 116 in fluid connection with the handle 150 and the port 158. In addition, the needle 114 may be attached to the device 100 so the needle 114 is at least partially within the lumen of the sheath 116. The needle 114 may be attached through the locking mechanism 156, the fastener 112, and/or through other means. The proximal zone 164 of the barrier 160 may be connected to the handle 150 to create a substantially complete seal, discouraging the flow of biological materials through the proximal opening of the barrier 160. This may be accomplished through various means of fastening or otherwise connecting the handle 150 and the barrier 160. For example, in certain implementations, the handle 150 and barrier 160 may have complimentary threads and the two pieces are screwed together. Certain implementations may include an adhesive or mechanical fastener configured to connect the handle 150 and barrier 160. In certain implementations, the connection is not between the handle 150 and the barrier 160 but is instead between other components, such as the barrier 160 and the sheath 116. These and other connections may be made or configured to provide strain relief in order to resist damaging the connections or materials during use.

As a specific example, an adult patient may have been selected for a lumbar puncture procedure by a doctor. Based on the patient's history and desired diagnostic criteria, the doctor may choose a handle 150 having a port 158 for collecting CSF, and an 18-gauge needle 114 having an atraumatic tip 118 with a 8-degree bend to reduce trauma to the patient. Because the patient has a spinal deformity, the doctor may need multiple attempts before successfully extracting CSF, so the doctor selects a frustoconical barrier 160 with a comparably large distal zone 162.

Preparing the Procedure 404

Preparing the procedure 404 may include performing various preparatory steps to make the subject, a health care provider, and the procedure space ready for the procedure. This may include sterilizing one or more surfaces or devices. The doctor may apply a numbing agent to the surgical site to decrease the discomfort of the subject.

Continuing the previous example, the doctor may place the patient in a lateral recumbent position and bring the patient's knees and chest together. In some situations, the patient may be placed in prone or seated positions. The doctor may wear protective gear, including gloves, a gown, and a mask. The doctor sterilizes the procedure area using an antiseptic, such as iodine, and isolates the procedure area using a sterile drape. The doctor also applies a numbing agent to lessen discomfort to the patient. For this particular procedure, the doctor may use an imaging device to provide visualization of the procedure area.

Deploying the Barrier 406

Deploying the barrier 406 may include using the barrier 160 to create the boundaries of the environment 170. In certain embodiments, this may be accomplished by covering the distal and proximal openings of the barrier 160 in order to create the environment 170 therebetween. For example, the proximal zone 164 may be attached to the handle 150 or other portion of the device 100. In certain embodiments, the distal zone 162 may be attached to the skin or other tissue of the subject. The particular tissue of the subject may be located near a surgical site. The location may be determined by visual, physical, or other inspection.

Figure 5A:
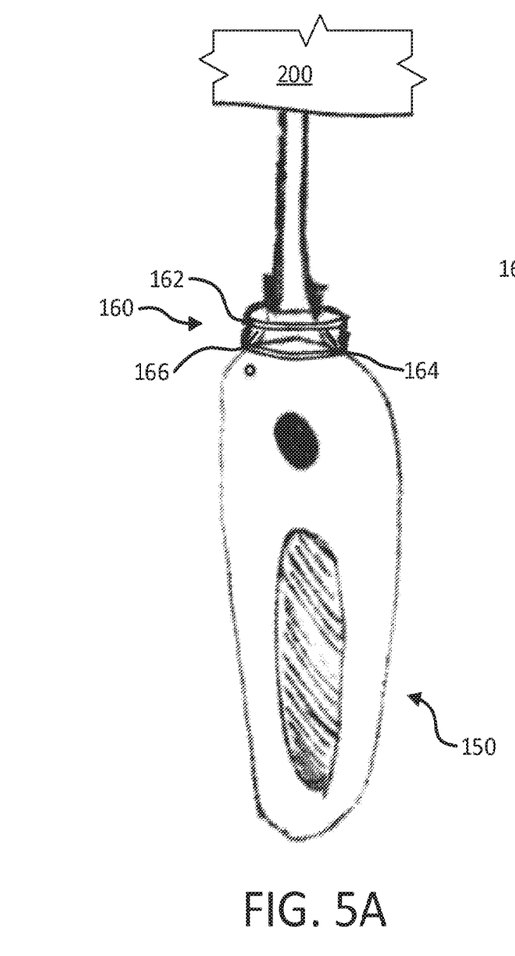
FIGS. 5A-C illustrates the expansion of the barrier from a collapsed to an expanded configuration according to certain implementations.
Figure 5B:
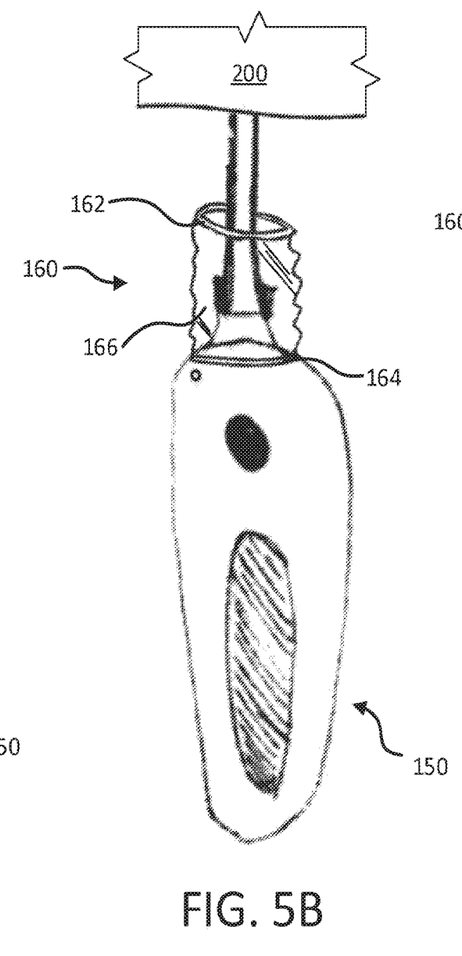
Figure 5C:
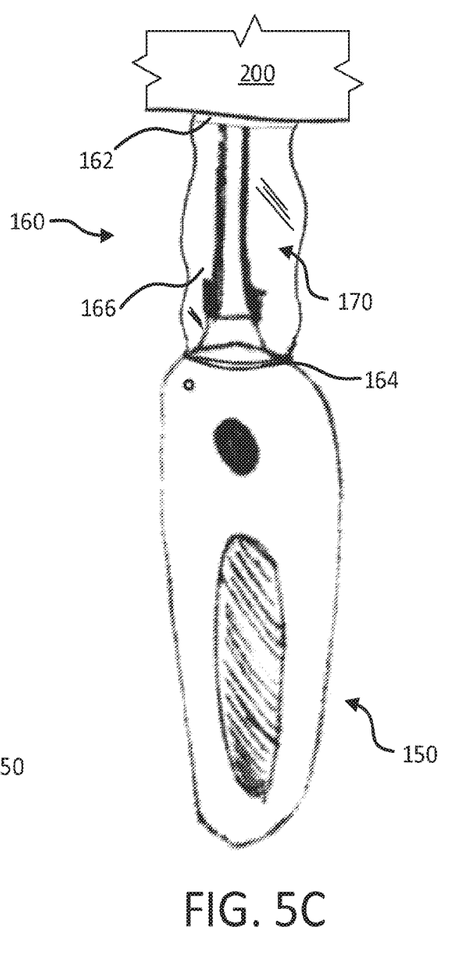

FIGS. 5A-5C illustrate the expansion of the barrier 160 from a collapsed to an expanded configuration according to certain implementations. FIG. 5A illustrates the barrier 160 in a collapsed state at the handle 150, and having a substantially sealed proximal end. In this illustration, the distal ends of the needle 114 and the sheath 116 have already been inserted into a tissue 200 of a subject. In certain other implementations, though, the barrier 160 may be deployed first and then the needle 114 and sheath 116 are inserted. FIG. 5B illustrates the barrier in a partially expanded configuration as the distal zone 162 extends toward the tissue 200. FIG. 5C illustrates the distal zone 162 affixed to the tissue 200, thereby substantially sealing the distal opening. The distal zone 162 may be attached to the tissue 200 by, for example, an adhesive strip or other fixation means located on the distal zone 162. In certain embodiments, the distal zone 162 is not directly attached to the tissue 200, but is instead attached to an introducer or other device. With both the distal and proximal openings substantially sealed, a particular environment 170 is created within the boundaries of the barrier 160.

In certain implementations, the barrier 160 may have a protective or other covering that maintains a condition of the barrier 160 or substantially prevents the barrier 160 from leaving the collapsed configuration. If the protective covering is in place, the covering may need to be removed before the barrier 160 can be deployed.

Continuing the example, the doctor may deploy the barrier 406 by removing a protective covering from the barrier 160, moving the barrier 160 from a collapsed to an expanded configuration by untwisting the barrier 160, peeling off a covering protecting an adhesive strip on the distal zone 162, and pressing the expanded barrier 160 against the skin of the patient. The doctor determines the particular placement location through physical inspection of the patient and the use of the imaging device.

Deploying the Needle and Sheath 408

Returning to FIG. 4, the step of deploying the needle and sheath 408 may include inserting the needle 114 and sheath 116 into a desired anatomical region of the subject. This may be done before, after, or contemporaneously with deploying barrier 406. Locations may include but are not limited to blood vessels, the subarachnoid space, internal bodily cavities (for example, the abdominal cavity, such as during a peritoneal tap or the thorax for pericardiocentesis) and other locations. This step 408 may include ensuring proper placement between the sheath 116 and the needle 114. As described above, the sheath 116 may be located at least partially around the needle 114 and/or inserted at least partially through the needle 114. To locate the sheath 116 around the needle 114, the needle 114 may be pushed through the sheath 116. To locate the sheath 116 within the needle 114, the sheath 116 may be inserted through a lumen of the needle 114. One or both of the needle 114 and sheath 116 may be affixed together, to the handle 150, or to another device by the proximal ends.

With the needle 114 and sheath 116 in the proper relationship, they may be deployed into the subject. For example, tip 118 of the needle 114 may be used to puncture the skin of the subject. Pressure may be applied until the distal end of the needle 114 is located near a desired anatomical location. In this manner, the distal ends of the sheath 116 and the needle 114 may be deployed to substantially the same anatomical location at substantially the same time using substantially the same action.

Maintaining the proper relative positioning of the needle 114 and the sheath 116 (e.g., so the sheath 116 does not slip while being inserted) may be accomplished in various ways. For example, the sheath 116 may be substantially stiff so as to resist bunching or slipping. In another embodiment, an angled tip 118 may discourage slippage. In another embodiment, the sheath 116 may be affixed to a hook, catch, or latch on the needle 114 to resist movement.

In certain embodiments, a stylet 124 may be used to facilitate the proper positioning of the sheath 116 during insertion. A portion of the sheath 116 may be inserted through the inner lumen of the needle 114 until the distal end of the sheath 116 is at or near the distal end of the needle 114. In certain implementations, the sheath 116 may be extended out of the distal end of the needle 114 and folded or rolled over the tip 118 of needle 114. The fold may discourage slippage of the sheath 116. Once the sheath 116 is in place, the stylet 124 may be inserted through the sheath 116 within the needle 114. In certain embodiments, the tip of the stylet 124 extends out of the tip 118. In certain other embodiments, the stylet 124 is extended only partially through the sheath 116, enough to provide stiffness and discourage slippage. The stylet 124, sheath 116, and internal lumen of the needle 114 may be sized such that the inserted stylet 124 discourages slippage of the sheath 116 within the internal lumen of the needle 114. This may be accomplished by, for example, causing the sheath 116 to press against a wall of the internal lumen of the needle 114.

In certain implementations, the stylet 124 may be used as a guide wire but need not be. The stylet 124 may be extended through the inner lumen of the needle 114, which, in turn, is inserted through the inner lumen of the sheath 116 (or vice versa). In implementations using a solid needle 114 that does not have an inner lumen, the stylet 124 may be placed between the needle 114 and the sheath 116. The stylet 124 may then be inserted near the anatomical location, and used to guide the rest of the components into position. Any suitable material, including metal or polymer, may be used for the stylet 124.

The insertion of the sheath 116 and the needle 114 may be accomplished at the same time or substantially the same time. For example, both the sheath 116 and needle 114 may be inserted at substantially the same time with a single motion.

Returning to the example, the doctor may insert the needle 114 through the sheath 116 and rely on the stiffness of the sheath 116 to prevent slippage. The doctor may grab the device 100 by the handle 150 using the grip 152 and press the tip 118 of the device 100 into the surgical site. The doctor may look through the semi-transparent barrier 160 to see where the device 100 is inserted. The doctor inserts the distal end 120 of the device 100 into a desired space, such a space between the L4 and L5 vertebrae of the patient's lumbar spine or other desired location. The distal end 120 is inserted through the patient's skin 200, through the supraspinous ligament, through the ligamentum flavum, and into the subarachnoid space.

Removing the Needle 410

The step of removing the needle 410 may be accomplished in various ways, depending on the relationship between the needle 114 and the sheath 116 and the type of the procedure. For example, the needle 114 may be unlocked by a press of the button 154. After the needle 114 is disengaged, the needle 114 may be removed through an opening in the handle 150. In certain embodiments, the button 154 may be used to disengage the fastener 122 from the locking mechanism 156. In such embodiments, the handle 150 may be separated from the needle 114 and sheath 116, exposing the proximal end of the needle 114. The needle 114 may then be removed by grasping and pulling the proximal end of the needle 114. In embodiments where a stylet 124 is used, the stylet 124 may need to be removed after, before, or at the same time as the needle 114 is removed. In certain implementations, the device 100 may be configured to cause the needle 114 to retract into the handle 150 (for example, to avoid accidental needle stick injury). The device 100 may be configured to retract the needle in such a way that a second needle 114 or other component may be attached to the handle 150 without the first needle 114 being in the way or otherwise blocking access.

Continuing the example, the doctor may press the button 154 on the handle 150 to cause the needle 114 to be retracted, such as by pulling, springing or by other action, into the handle 150. Because the doctor is performing a lumbar puncture, the selected handle 150 may be configured to retract the needle 114 slowly, or at any desired rate.

Performing the Procedure 412

In the step of performing the procedure 412, a procedure may be conducted within or through the sheath 116. The procedure may take various forms and may include but is not limited to percutaneous surgery (e.g., placing electrostimulation leads on or near the spinal cord, insertion of a catheter through the sheath 116, delivery of stent into a blood vessel, and other procedures), removal or treatment of CSF, laparoscopic surgery, peritoneal taps for ascites, thoracentesis for pleural effusion, and other procedures. In certain implementations, the device 100 may be customized or otherwise configured for the particular procedures. For example, if the device 100 is to be used in a thoracentesis, the device 100 may be configured to allow the handle 150 to be detached and a 3-way stopcock to be applied in its place (e.g., for aspirating or deploying fluid).

Depending on how the process 400 was conducted, the handle 150 and the sheath 116 may be attached during this step 412 and the procedure may be performed using a portion of the handle 150. For example, the port 158 of the handle 150 may be used for the collection of CSF or other bodily fluids (e.g., for analysis or disposal) or may be configured to be an access point through which devices are inserted. For instance, a volume of CSF may be removed through the port 158, processed, and reintroduced through the same or a different port 158. The handle 150 may include a manometer to measure pressure of, for example, CSF. In certain embodiments, the barrier port 168 may be used for access to the procedure site during the procedure.

Continuing the example, the doctor may attach a manometer to the port 158 to measure the pressure of the patient's CSF. After taking the measurement, the doctor may remove the manometer and use the port 158 to collect a sample of CSF for analysis.

Within this disclosure, directional references (e.g., proximal and distal) are used for identification purposes to aid the reader's understanding and do not necessarily create limitations as to the position, orientation, or use of the invention. Connection references (e.g., attached, coupled, connected, and joined) may include intermediate members between a collection of components and relative movement between components. Such references do not necessarily infer that two components are directly connected and in fixed relation to each other. The exemplary drawings are for purposes of illustration only and the dimensions, positions, order and relative sizes reflected in the drawings attached hereto may vary.

The above specification provides a complete description of the structure and use of exemplary embodiments as claimed below. Although various embodiments of the invention as claimed have been described above with a certain degree of particularity, or with reference to one or more individual embodiments, those skilled in the art could make numerous alterations to the disclosed embodiments without departing from the spirit or scope of this disclosure. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the disclosure as defined in the following claims.

What is claimed is:

1. A medical device comprising:
   a handle including a proximal end and a distal end, and including a locking mechanism disposed on the distal end of the handle;
   a needle having a proximal end releasably secured to the distal end of the handle with the locking mechanism;
   a sheath disposed around the needle, a proximal end of the sheath including a fastener, the sheath being releasably secured to the distal end of the handle by the fastener; wherein the needle and the sheath are designed to be maintained in a first configuration in which the needle and the sheath are configured to be simultaneously introduced through a patients skin and into a subarachnoid space, and a second configuration in which the needle is removed from the sheath; and
   a barrier comprising a collapsible sleeve disposed around the sheath and the needle, the barrier having a proximal zone and a distal zone connected by a covering, the proximal zone being secured to the distal end of the handle, and the distal zone including an attachment feature configured to releasably attach the distal zone to a skin surface.

2. The medical device of claim 1, wherein the locking mechanism comprises a Luer fitting or a 3-way stopcock.

3. The medical device of claim 1, wherein the needle comprises a tip having an angle.

4. The medical device of claim 3, wherein the angle of the tip is between 5 and 10 degrees.

5. The medical device of claim 1, wherein the handle further comprises a port in fluid connection with an inner lumen of the sheath.

6. The medical device of claim 1, wherein the sheath comprises a braided material.

7. The medical device of claim 1, wherein the handle further comprises a button for operably controlling a locking mechanism to release the needle from connection to the distal end of the handle.

8. The medical device of claim 1, wherein the handle is egg-shaped.

9. The medical device of claim 1, wherein the barrier is longitudinally extendable and collapsible relative to the needle.

10. The medical device of claim 1, wherein the barrier is capable of transitioning from an extended configuration to a collapsed configuration.

11. The medical device of claim 1, wherein the barrier includes a collapsed configuration, and an expanded configuration, wherein when the barrier is in the expanded configuration, the proximal zone is separated from the distal zone by a first distance, and when the barrier is in the collapsed configuration, the proximal zone is separated from the distal zone by a second distance which is less than the first distance.

12. The medical device of claim 1, wherein the attachment feature comprises an adhesive strip.

13. The medical device of claim 1, wherein the barrier includes pleats or folds.

14. The medical device of claim 1, wherein a space is defined between an outer surface of the sheath and an inner surface of the barrier.

15. The medical device of claim 1, wherein the barrier includes a distal opening, a proximal opening, and a barrier port defined through the collapsible sleeve.

* * * * *